US012352343B2

(12) United States Patent
Spuhler et al.

(10) Patent No.: US 12,352,343 B2
(45) Date of Patent: Jul. 8, 2025

(54) MECHANISM FOR HANDLING A SURGICAL INSTRUMENT

(71) Applicants: ACUSURGICAL, Montpellier (FR); CENTRE NATIONAL DE LA RECHERCHE SCIENTIFIQUE, Paris (FR); UNIVERSITE DE MONTPELLIER, Montpellier (FR)

(72) Inventors: Christoph Spuhler, Montpellier (FR); Yassine Haddab, Montpellier (FR); Philippe Poignet, Gignac (FR); Antoine Morel, Montpellier (FR); Alonso Sanchez, Juvignac (FR)

(73) Assignees: ACUSURGICAL, Montpellier (FR); CENTRE NATIONAL DE LA RECHERCHE SCIENTIFIQUE, Paris (FR); UNIVERSITE DE MONTPELLIER, Montpellier (FR)

( * ) Notice: Subject to any disclaimer, the term of this patent is extended or adjusted under 35 U.S.C. 154(b) by 453 days.

(21) Appl. No.: 17/997,359

(22) PCT Filed: Apr. 30, 2021

(86) PCT No.: PCT/EP2021/061440
§ 371 (c)(1),
(2) Date: Oct. 27, 2022

(87) PCT Pub. No.: WO2021/219864
PCT Pub. Date: Nov. 4, 2021

(65) Prior Publication Data
US 2023/0193988 A1 Jun. 22, 2023

(30) Foreign Application Priority Data
Apr. 30, 2020 (FR) ...................... 2004320

(51) Int. Cl.
*F16H 37/12* (2006.01)
*F16H 37/16* (2006.01)
*A61F 9/007* (2006.01)

(52) U.S. Cl.
CPC ......... *F16H 37/122* (2013.01); *F16H 37/124* (2013.01); *F16H 37/16* (2013.01); *A61F 9/007* (2013.01)

(58) Field of Classification Search
CPC ....... F16H 37/122; F16H 37/124; F16H 37/16
See application file for complete search history.

(56) References Cited

U.S. PATENT DOCUMENTS 5,078,140 A * 1/1992 Kwoh .................... A61B 34/30
901/41
5,257,998 A * 11/1993 Ota ........................ A61B 90/11
901/41

(Continued)

FOREIGN PATENT DOCUMENTS

WO 2019/183236 A1 9/2019

OTHER PUBLICATIONS

International Search Report for PCT/EP2021/061440 (Jun. 30, 2021).

*Primary Examiner* — Nathaniel C Chukwurah
(74) *Attorney, Agent, or Firm* — Merchant & Gould P.C.

(57) ABSTRACT

An actuation mechanism for a surgical instrument (100) includes a sleeve (202) configured to receive the surgical instrument and including one or more parts (208, 210, 226), with studs (250, 252) provided on each part, on some parts only, or distributed over the different parts. At least two wheels (204, 206) are mounted on the sleeve on either side of the part or parts, each wheel being equipped with at least one groove (242) and a mechanical transmission element (244). The groove of each wheel movably receives one of the studs in the groove. At least two drive shafts (212, 214), (Continued)

each being equipped with a first mechanical transmission element (254), cooperate with the mechanical transmission element (244) of one of the wheels.

19 Claims, 13 Drawing Sheets

(56) References Cited

U.S. PATENT DOCUMENTS

| | | | | |
|---|---|---|---|---|
| 5,273,039 A | * | 12/1993 | Fujiwara | G02B 21/0012 |
| | | | | 600/407 |
| 5,807,378 A | * | 9/1998 | Jensen | B25J 15/04 |
| | | | | 606/1 |
| 2018/0014849 A1 | | 1/2018 | Scheller et al. | |

* cited by examiner

[Fig.1]
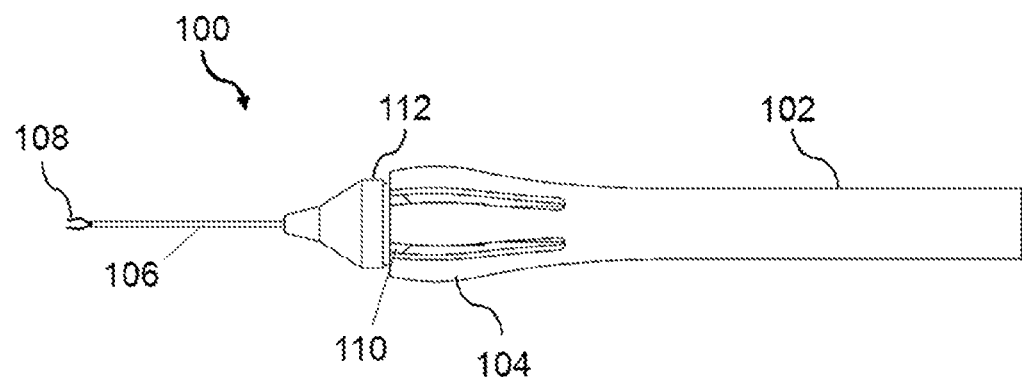

[Fig.2]
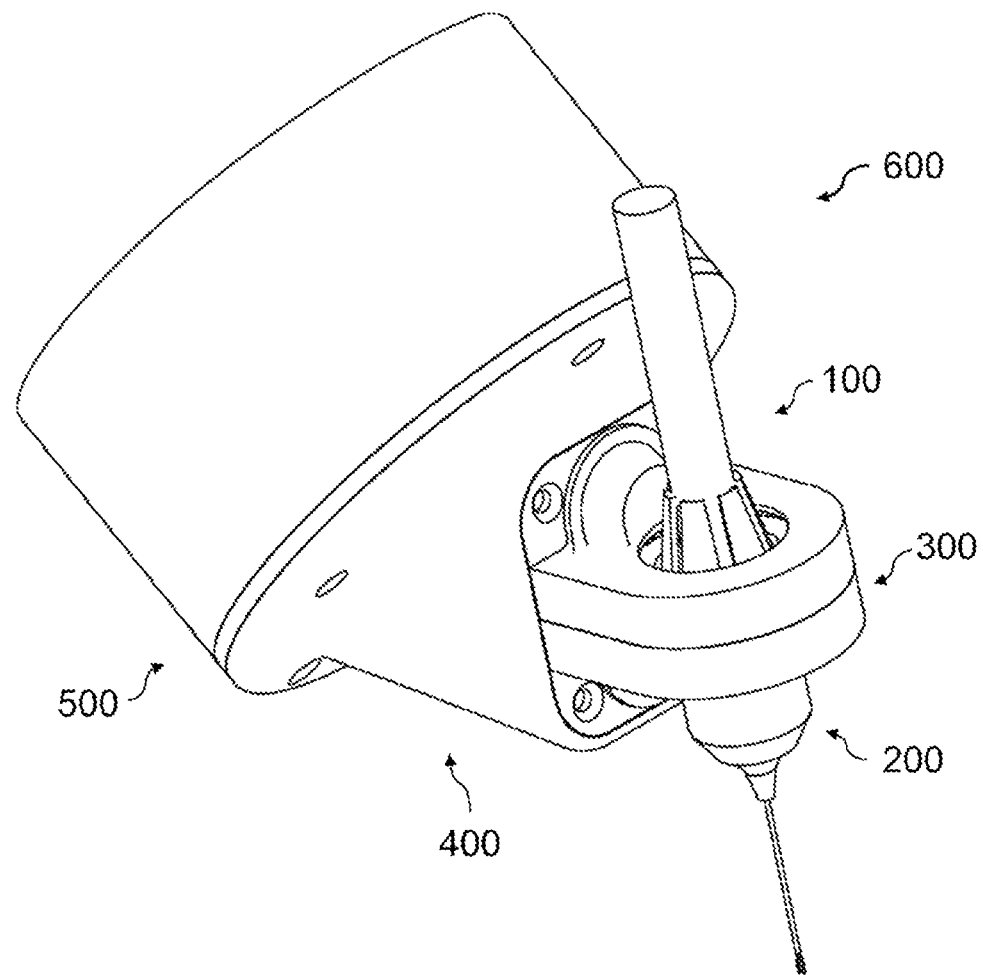

[Fig.3]
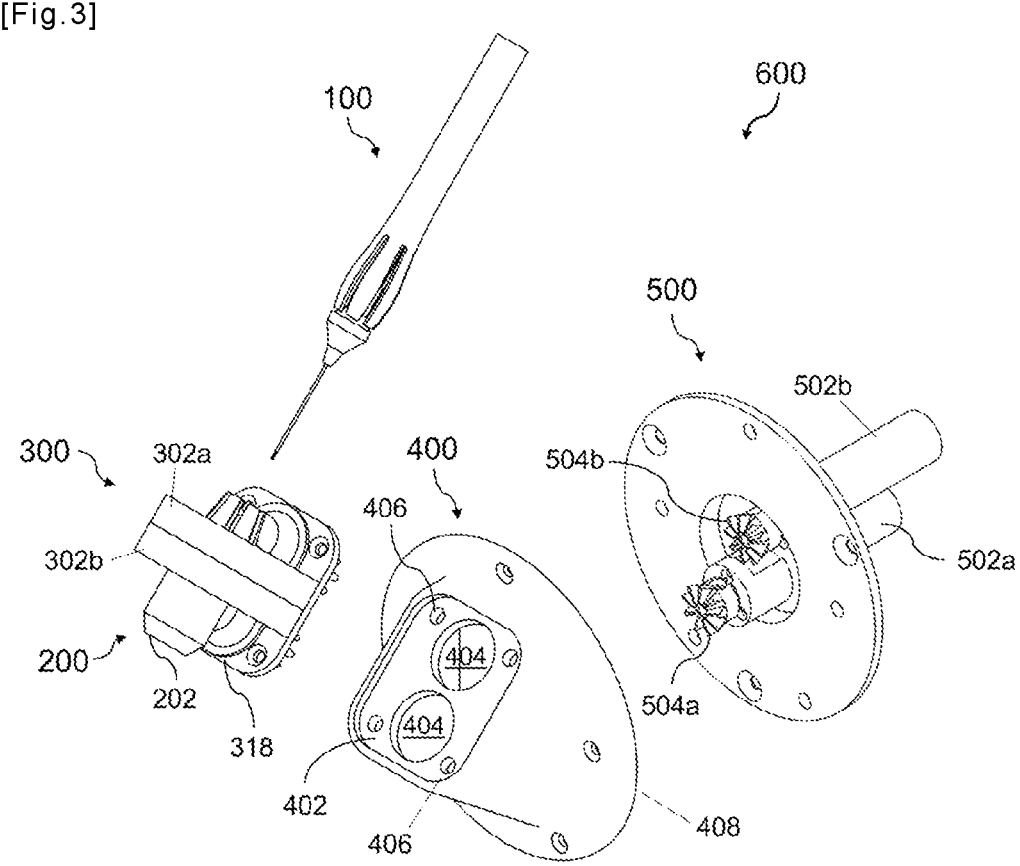

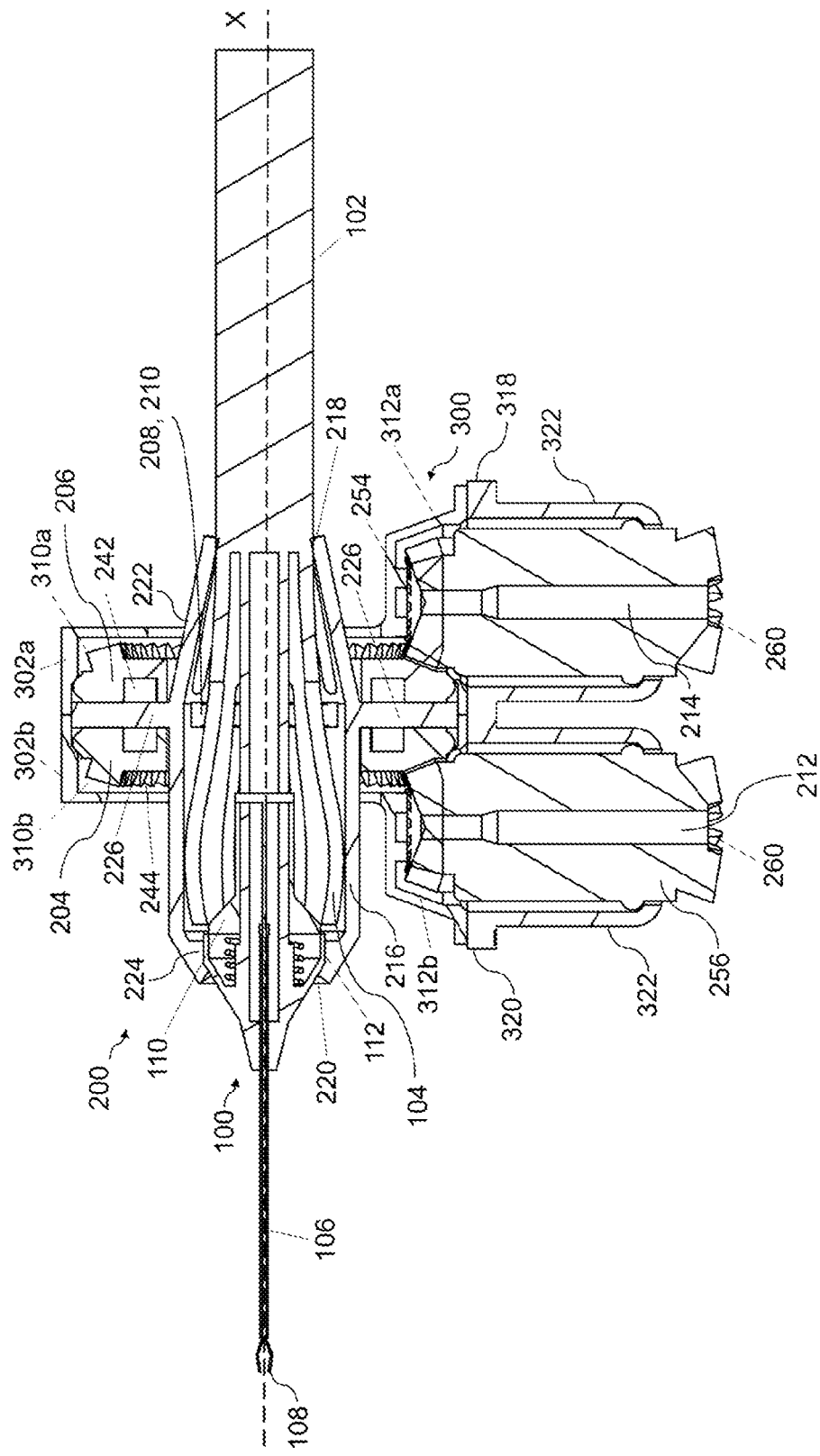
[Fig. 4]

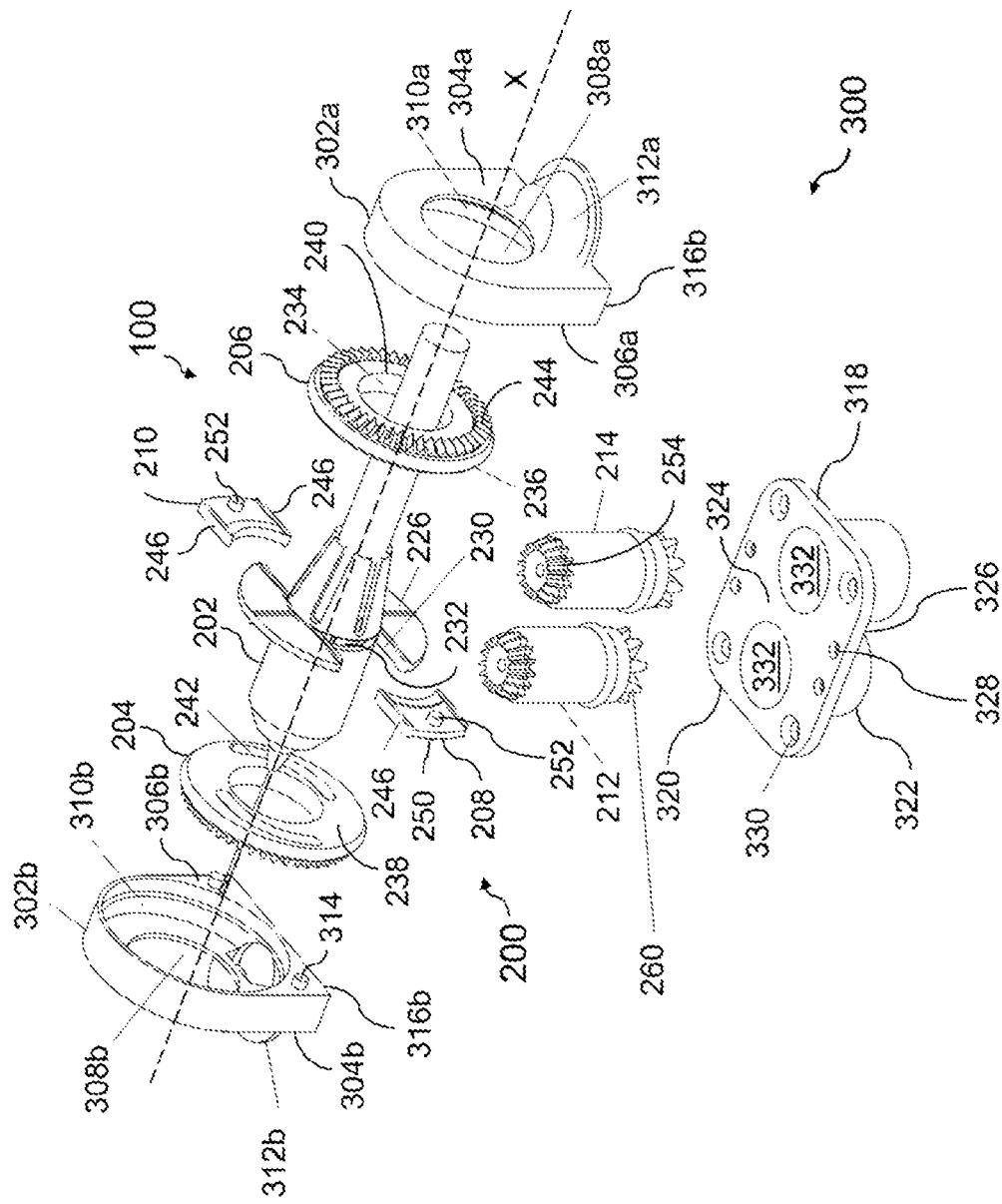
[Fig.5]

[Fig.6A]
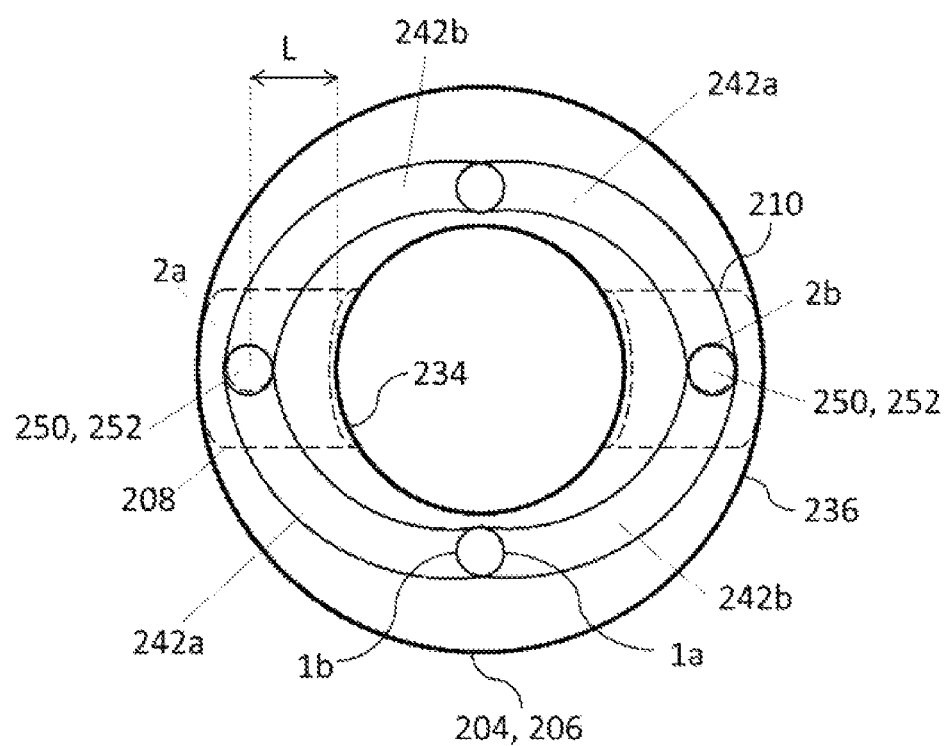

[Fig.6B]
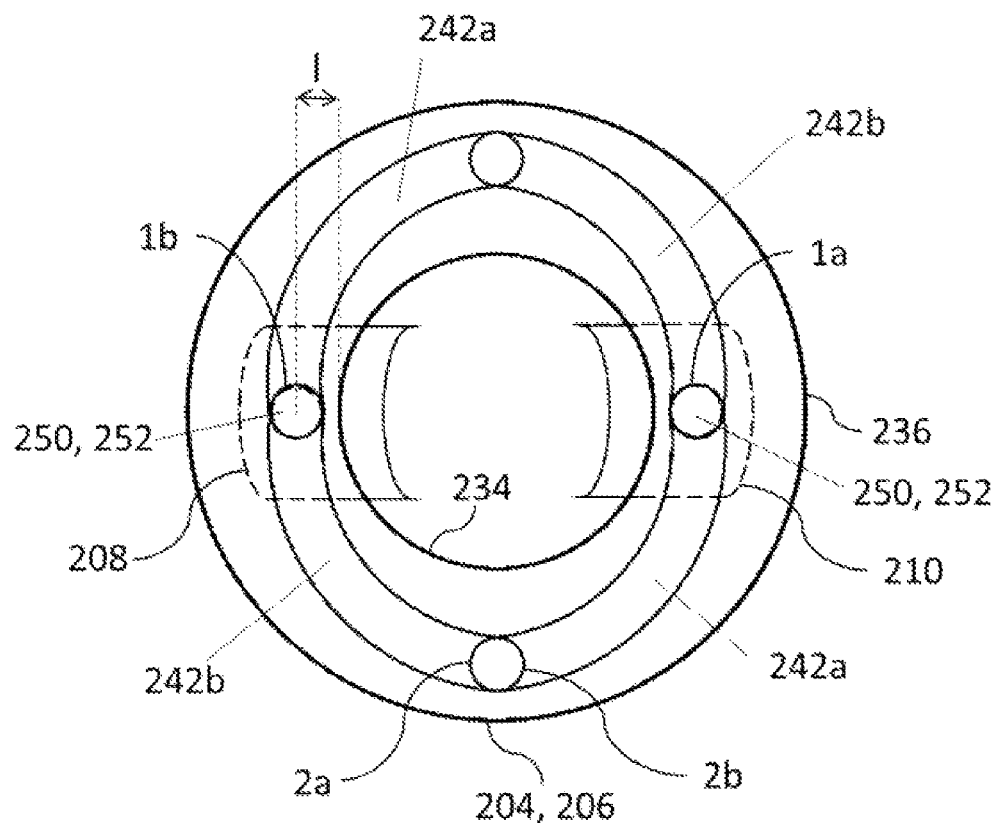

[Fig.6C]
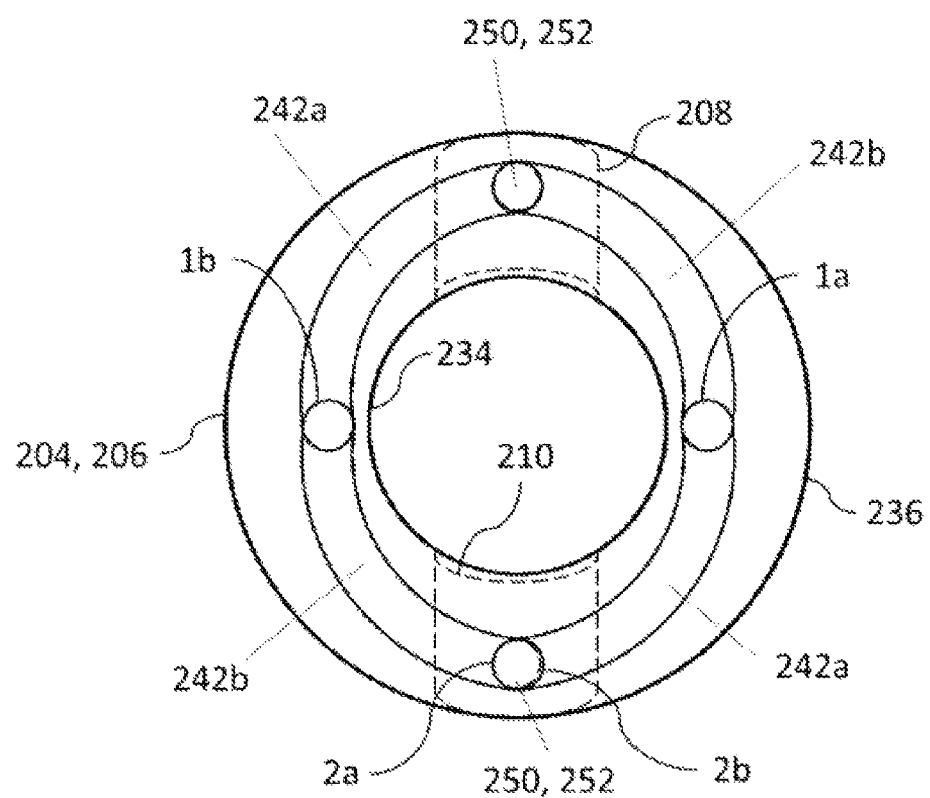

[Fig.7A]
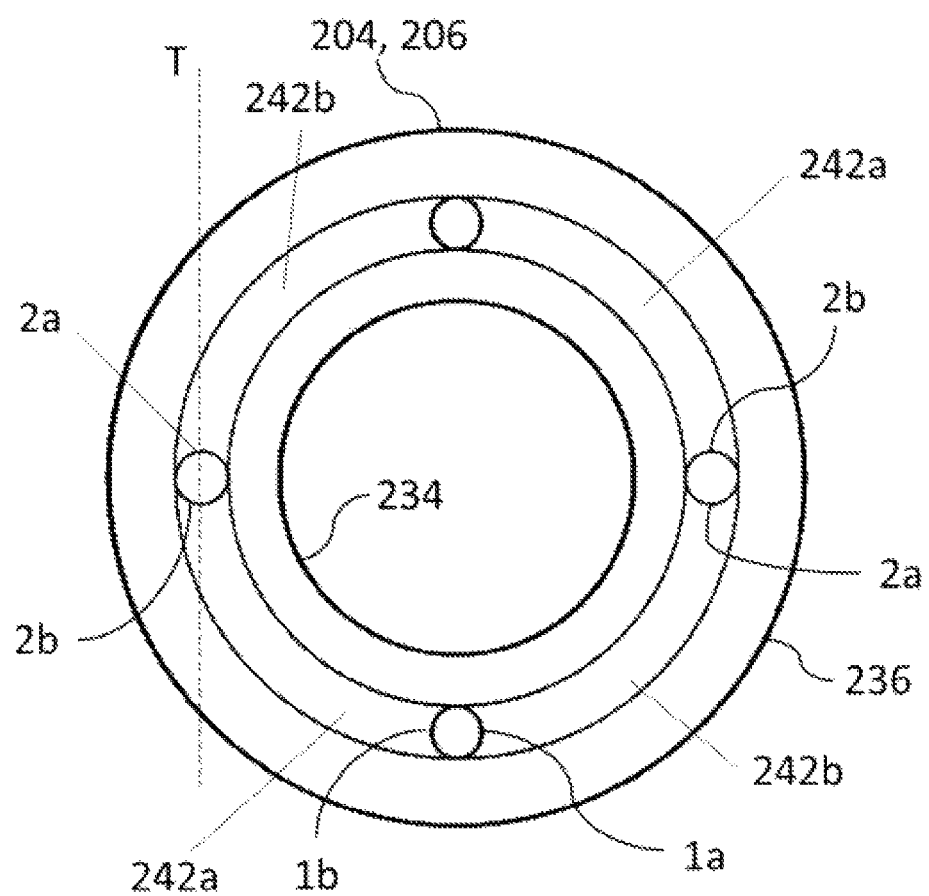

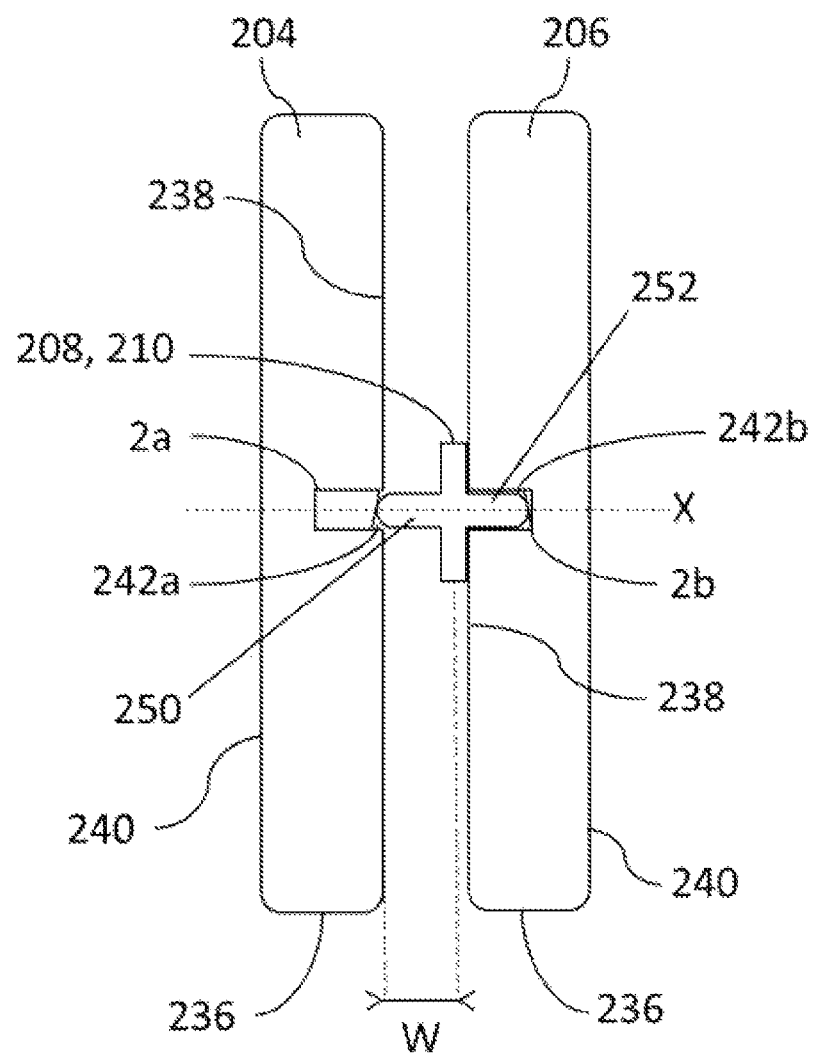
[Fig.7B]

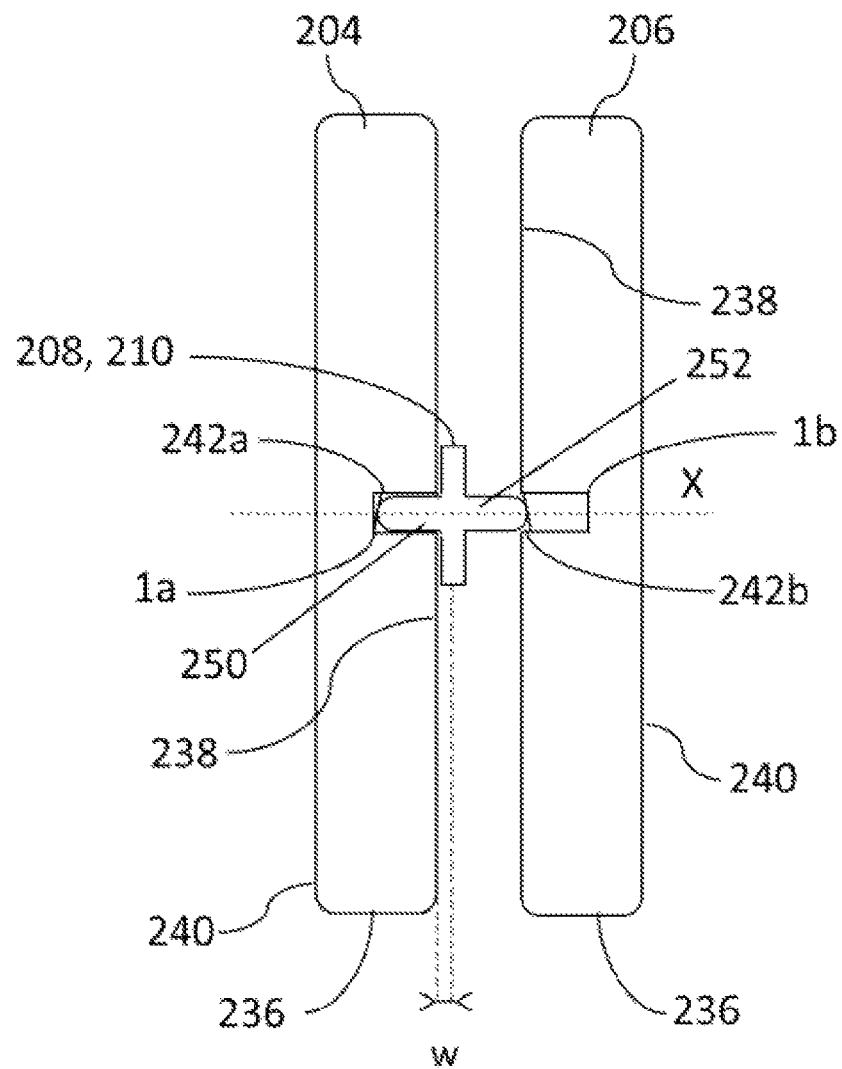
[Fig.7C]

[Fig. 8]
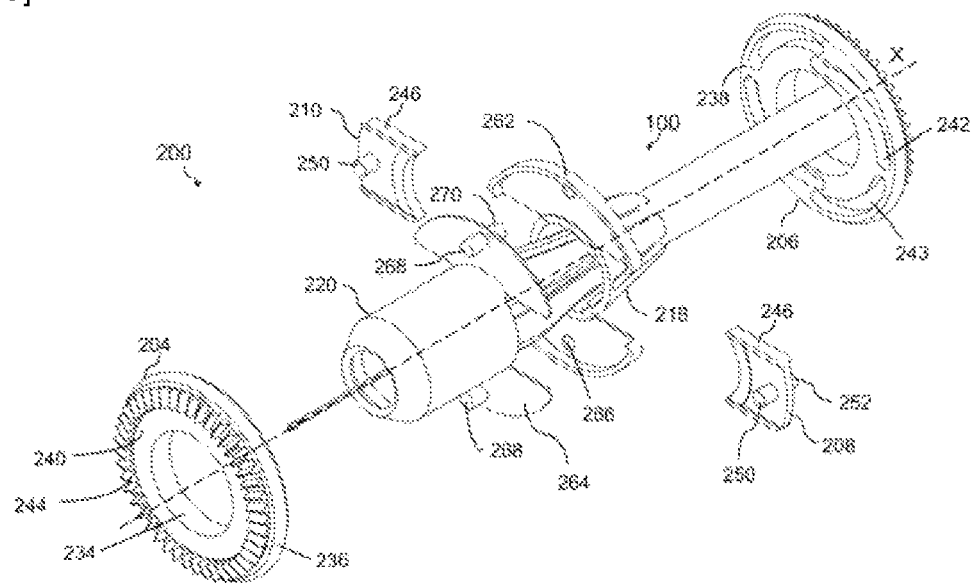

[Fig. 9]
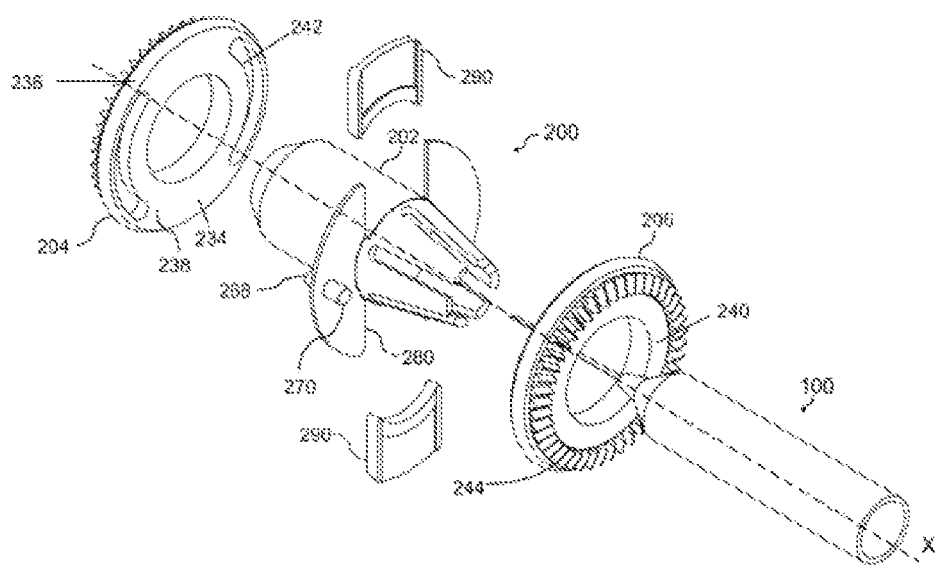

MECHANISM FOR HANDLING A SURGICAL INSTRUMENT

This application is a National Stage Application of PCT/EP2021/061440, filed Apr. 30, 2021, which claims benefit of Patent Application No. 2004320, filed Apr. 30, 2020 in France, which applications are incorporated herein by reference. To the extent appropriate, a claim of priority is made to each of the above-disclosed applications.

TECHNICAL FIELD OF THE INVENTION

The present invention relates to an actuation mechanism for a surgical instrument intended to be used in a robotic platform for surgery, in particular eye surgery.

TECHNICAL BACKGROUND

It is well known technically that a vitreoretinal surgery operation, or commonly eye surgery, is carried out by a practitioner on a patient through a cannula, or trocar, placed on the front of the eye and into which a surgical instrument is inserted. This trocar defines an access that allows us in particular to cross the vitreous and reach the posterior portion of the eye, where the retina is located.

"Instrument" means a device as shown in FIG. 1. Typically, a typical instrument 100 for eye surgery comprises a handle 102, a gripper 104, a sheath 106 and a tool 108.

The handle 102 is configured to fit in a hand of the practitioner so that the practitioner has a good grip. The gripper 104, located in the extension of the handle 102, is designed for the practitioner to position his or her fingers on to manipulate the instrument 100. In addition, the gripper 104 may deform as a result of a pressure exerted by the practitioner. The deformation of the gripper 104 results in the displacement of a pusher element 110, located inside a conical head 112, which actuates the sheath 106. The sheath 106 slides along the tool 108 located at its end, allowing it to be actuated in the event that the tool 108 is intended for a pinch function, such as a pliers or a pair of scissors. A return member, such as a spring, is housed in the head 112 and cooperates with the pusher element 110, allowing the actuated tool 108 to return to its initial configuration when the pressure on the gripper 104 is released.

The tool is the functional portion of the instrument and can take various forms. The tool can be a pliers, a pair of scissors, a knife, a hoover, a laser, a cryogenic probe or anything else that can be used in surgery.

In one embodiment, the gripper 104 is equipped with a slide system that performs a translational movement to actuate the tool 108.

In another embodiment, the instrument 100 is of the backflush type and the gripper 104 is equipped with a pusher button allowing a sucking action with the tool 108.

The practitioner manipulates the instrument in space, but has to be particularly dexterous in order to produce movements with a very small amplitude of only a few tens of micrometres.

However, a manual intervention presents many risks for the patient, mainly related to a manipulation error by the practitioner.

In order to provide more comfort, precision and safety during an eye surgery, a robotization of this eye surgery is being considered. To achieve this, it is necessary that the mechanisms for manipulating and actuating the surgical instruments reproduce movements similar to those of the practitioner using a surgical instrument.

In the document WO 2019/183236 A1, a surgical instrument is installed on a base that allows rotational and translational movements. However, such apparatus has the disadvantage of being bulky and impractical, since it requires, for example, the prior installation of a collar on the instrument, and does not allow for to manipulation of all types of tools that can be used for a surgery of the eye. In addition, this apparatus does not allow to eliminate the risk of the instrument sliding towards the eye in the event of dissociation from its base.

SUMMARY OF THE INVENTION

The present invention aims to solve at least one of the above-mentioned disadvantages. In particular, the present invention aims to propose a mechanism allowing for manipulating and actuating a surgical instrument in a safe, practical, precise and efficient manner.

To this end, the invention proposes an actuation mechanism for a surgical instrument comprising:
- a sleeve, equipped with a longitudinal axis X, configured to receive the surgical instrument and comprising one or more parts extending substantially in a plane perpendicular to said longitudinal axis X, a plurality of studs extending along the longitudinal axis X being provided on the or each part, on some parts only, or distributed over the different parts;
- at least two wheels, mounted on the sleeve on either side of said part or parts along said longitudinal axis X, each wheel being equipped with at least one groove and a mechanical transmission element, said at least one groove of each wheel receiving, in a movable manner in said groove, one of said plurality of studs;
- at least two drive shafts, a first drive shaft being equipped with a first mechanical transmission element cooperating with the mechanical transmission element of one of the two wheels and a second drive shaft being equipped with another first mechanical transmission element cooperating with the mechanical transmission element of the other of the two wheels.

Thus, the invention ensures that a movement of the surgical instrument is identical to an ordinary movement performed by a practitioner. The mechanism allows the surgical instrument to be manipulated with several degrees of freedom, in particular in rotation and in translation, but also allows any variant of gripper of the instrument to be actuated. This confers the advantage that a wide range of standard, off-the-shelf surgical instruments can be used without requiring a hardware modification of the latter.

In addition, the invention ensures increased safety for the patient. Indeed, the mechanism allows a high degree of precision in the displacement of the surgical instrument which is maintained forward by the mechanism, thus preventing any accidental sliding of the instrument towards the patient and in particular towards the eye.

Again, the invention ensures an improved integration of the manipulation mechanisms and thus a small workspace clutter, allowing the practitioner to keep the patient in his or her field of vision and, in addition, allowing the use of other apparatus in the vicinity, such as a microscope or other apparatus similar to the invention.

The actuation mechanism according to the invention may comprise one or more of the following characteristics, taken alone or in combination with each other:
- the groove is provided on a first face and the mechanical transmission element is located on a second face of each wheel;

the groove and the mechanical transmission element are located on the same face of the wheel;

the sleeve comprises an internal abutment extending radially at the level of a first end of said sleeve, and flexible tongues extending axially at the level of a second end;

the at least one part is a jaw, mounted between guides so as to be translatable relative to the guides, the guides themselves being mounted stationary relative to the sleeve;

the at least one part is a guide, stationary mounted with respect to the sleeve;

the mechanical transmission element is a gear or a belt driven pulley;

the groove has a radial distance with respect to the centre of the wheel that varies along the groove;

the groove has a radial distance with respect to the centre of the wheel which is constant along the groove;

the groove has a variable depth along the groove each wheel comprises at least one first groove having a radial distance with respect to the centre of the wheel which varies along the first groove and having a variable depth along the first groove, and at least one second groove, different from the first groove, having a radial distance with respect to the centre of the wheel which is constant along the second groove and having a variable depth along the second groove.

The present invention also relates to a module characterised in that it comprises an actuation mechanism as described above, the mechanism being housed in a protective compartment, maintaining the elements of the actuation mechanism in interaction.

The module according to the invention may comprise one or more of the following characteristics, taken alone or in combination with each other:

it comprises a removable receptacle configured to receive the protective compartment, the receptacle being attached to one end of an apparatus;

at least two parallel drive shafts, mechanically connected to a motorisation element, project from the end of the apparatus, each shaft being configured to cooperate with a second mechanical transmission element of one of the at least two drive shafts of the actuation mechanism;

a protective cover is integrated into the receptacle so that the cover surrounds a portion opposite the module;

the receptacle, the compartment, the mechanism and the cover are sterile, single-use equipment.

The present invention also relates to a method for implementing an actuation mechanism as described above, the method being carried out outside the patient, wherein a rotation in the same direction of the wheels causes a rotation of the sleeve about its longitudinal axis.

The present invention also relates to a method for implementing an actuation mechanism as described above, the method being carried out outside the patient, wherein a rotation in opposite directions of the wheels causes a radial translation of at least one part so that the part exerts a pressure on the surgical instrument.

The present invention also relates to a method for implementing an actuation mechanism as described above, the method being carried out outside the patient, wherein a rotation in opposite directions of the wheels causes a longitudinal translation of at least one part along the surgical instrument.

The present invention also relates to a method for implementing an actuation mechanism as described above, the method being carried out outside the patient, wherein a rotation of the wheels in opposite directions simultaneously causes a longitudinal translation and a radial translation of at least one part so that said part exerts a pressure on the surgical instrument while displacing longitudinally along the surgical instrument.

The present invention also relates to a method for implementing an actuation mechanism as described above, the method being carried out outside the patient, wherein a rotation of the wheels in opposite directions simultaneously causes a longitudinal translation of at least one part along the surgical instrument and a radial translation of at least one other part such that the other part exerts a pressure on the surgical instrument.

BRIEF DESCRIPTION OF THE FIGURES

Further characteristics and advantages of the invention will become apparent from the following detailed description, for the understanding of which reference is made to the attached drawings in which:

FIG. 1 is a schematic profile view of a standard surgical instrument;

FIG. 2 is a schematic perspective view of a module carrying an actuation mechanism for the surgical instrument of FIG. 1, according to one embodiment of the invention;

FIG. 3 is an exploded schematic view of FIG. 2;

FIG. 4 is a schematic cross-sectional view of an actuation mechanism housed in a protective compartment;

FIG. 5 is a schematic perspective view of FIG. 4;

FIG. 6A is a schematic view of the differential cam mechanism in an open position of the jaws according to one embodiment of the invention;

FIG. 6B is a schematic view of the mechanism in FIG. 6A, after the wheels have been rotated simultaneously by a quarter turn in opposite directions;

FIG. 6C is a schematic view of the mechanism in FIG. 6A, after the wheels have been rotated simultaneously in the same direction by a quarter turn;

FIG. 7A is a schematic view of the differential cam mechanism in an initial position according to another embodiment of the invention;

FIG. 7B is a schematic view along a sectional axis of FIG. 7A;

FIG. 7C is a schematic view along the cross-sectional axis of FIG. 7A, after simultaneous quarter turn rotation of the wheels in opposite directions;

FIG. 8 is an exploded schematic perspective view of an actuation mechanism according to another embodiment; and FIG. 9 is an exploded schematic perspective view of an actuation mechanism in another embodiment.

DETAILED DESCRIPTION OF THE INVENTION

In the following detailed description, reference is made to a device intended for use during surgery. It should be noted that the examples of embodiments described are all carried out outside any surgical operation and therefore outside the patient.

In the following, reference is made to a standard surgical instrument similar to the instrument described above in FIG. 1.

Reference is now made to FIGS. 2 to 5, which illustrate a mechanism for actuating a surgical instrument according to one embodiment.

The surgical operations involving the eye can be carried out with the help of an apparatus or a robotic platform. The apparatus comprises motorisation elements that allow it to move with several degrees of freedom. In order to manipulate and actuate the surgical instrument 100 as a practitioner would, the apparatus may be equipped with a module 600 equipped with a mechanism 200 for actuating the instrument 100 which may be comprised in a protective compartment 300 attached to a receptacle 400 located at the end 500 of the apparatus.

The actuation mechanism 200 further comprises a sleeve 202, at least two movable wheels 204, 206, at least one part 208, 210, which will be referred to as a jaw, and at least two drive shafts 212, 214.

The sleeve 202 comprises a main body 216 of generally cylindrical shape, extending along a longitudinal axis X. The body 216 is recessed along this axis X and open at an upstream end 218 and a downstream end 220 so as to receive the instrument 100.

The upstream end 218 of the sleeve 202 comprises axially extending tongues 222 distributed radially about the longitudinal axis X. The tongues 222 are flexible so that they can deform and move apart as the instrument 100 passes through the sleeve 202.

The downstream end 220 of the sleeve 202 forms an annular constriction and has a radially extending internal abutment 224. This abutment 224 allows the surgical instrument 100 to be held forward when inserted into the sleeve 202.

It is understood that the surgical instrument 100 may be inserted into the sleeve 202 through the upstream end 218. Furthermore, the diameter of the downstream end 220 of the sleeve is substantially smaller than the diameter of the base of the head 112 of the instrument 100 so that the instrument 100 does not disengage from the mechanism 200 during use. This has the advantage of ensuring the safety of the patient. Indeed, the surgical instrument 100 is maintained forward by the internal abutment 224, thus preventing any accidental sliding of the instrument 100 towards the patient and in particular towards his eye.

The sleeve 202 also comprises at least one guide 226, stationary mounted with respect to the sleeve 202, for example came from matter with the sleeve 202, extending substantially in a plane P, perpendicular to the longitudinal axis X. In the embodiment shown here, the sleeve 202 comprises two guides 226, distributed equidistantly around the sleeve 202. Each guide 226 is equipped with two planar tracks 230 extending on either side of the sleeve 202 along an axis perpendicular to the longitudinal axis X. Each track 230 of a guide 226 faces the track 230 of the other of the two guides 226 so that the tracks 230 are parallel.

The sleeve 202 further comprises at least one peripheral opening 232 which is located on the periphery of the main body 216. In the embodiment shown here, the sleeve 202 comprises two openings 232. These openings 232, distributed equidistantly around the sleeve, extend circumferentially between the guides 226 and lie in the same perpendicular plane P as the guides 226. The width of the openings 232 may be substantially equal to or substantially greater than the width of the tracks 230 of the guides 226.

The two movable annular wheels 204, 206 are mounted axially on the sleeve 202 on either side of the guides 226. It is understood that the guides 226 also act as spacers between the wheels 204, 206. Each wheel 204, 206 has a longitudinal axis that coincides with the longitudinal axis X of the sleeve 202. Each wheel 204, 206 further comprises an internal peripheral edge 234 and an external peripheral edge 236, concentric and centred on the longitudinal axis X, a first face 238 and a second face 240, opposite to the first face, and oriented in the direction of the longitudinal axis X. The first face 238 comprises at least one groove 242, hollowed out into a non-zero segment of the thickness of the wheel 204, 206, and faces the guides 226. The groove 242 comprises two ends and describes a trajectory. This trajectory may for example, but not exclusively, be an arc, concentric or not with the wheel 204, 206. The second face 240 is equipped with a mechanical transmission element 244. In the embodiment shown here, the element 244 is a gear but may also be a pulley configured to be belt driven.

In one embodiment, not shown here, the groove 242 and the mechanical transmission element 244 may be located on a same face 238 of the wheel 204, 206. It is understood that the groove 242 and the mechanical transmission element 244 are located on the same face 238, the latter being located opposite the at least one guide 226.

In another embodiment, not shown, the mechanical transmission element 244 may be located on the external peripheral edge 236 of the wheel 204, 206.

The at least one jaw 208, 210, extends substantially in the plane P perpendicular to the longitudinal axis X. The jaw 208, 210 is mounted on the sleeve 202 so that it can translate relative to the at least one guide 226. The jaw 208, 210 further comprises two opposing tracks 246, each located on a slice of the jaw 208, 210 and whose width is substantially equal to the thickness of the jaw 208, 210. The tracks 246 of the jaw 208, 210 cooperate with the tracks 230 of the guides 226. In other words, the tracks 246 of the jaws 208, 210 slide on the tracks 230 of the guides 226.

It is understood that the width of the tracks 246 of a jaw is substantially less than or equal to the width of a track 230 of a guide 226. The width of the tracks 246 is also substantially less than the width of an opening 232. In other words, the width of the opening 232 is substantially greater than the thickness of the jaw 208, 210.

In the embodiment shown here, the mechanism 200 comprises two jaws 208, 210, equally distributed between the guides 226.

A first jaw 208 comprises a first axially oriented stud 250 on at least one face thereof, which is housed in the at least one groove 242 of a first wheel 204.

A second jaw 210, similar to the first jaw 208, comprises on at least one of its faces a second axially oriented stud 252, housed in the at least one groove 242 of the other wheel 206.

The first jaw 208 may comprise on its other face a further stud 252, axially oriented in the extension of the first stud 250, housed in a second groove 242 of the other wheel 206.

The second jaw 210 may comprise on its other face, another stud 250, axially oriented in the extension of the second stud 252, housed in a second groove 242 of the first wheel 204.

It is understood that each jaw 208, 210 may comprise one or more studs 250, 252, extending parallel to the longitudinal axis X of the sleeve 202. In one embodiment, each jaw 208, 210 comprises a stud 250 on a first face or a stud 252 on a second face. If the first jaw 208 comprise a stud 250 on its first face then the second jaw 210 comprise a stud 252 on its second face, and vice versa. In a second case, each jaw 208, 210 comprises a stud 250 on its first face and a stud 252 on its second face, in other words, one stud 250, 252 per face. In addition, each jaw 208, 210 may cooperate with one of the two wheels 204, 206 or with the two wheels 204, 206 via the stud or studs 250, 252, each cooperating with a groove 242.

The width of the groove 242 is substantially equal to or greater than the cross-section of the stud 250, 252 of the jaw 208, 210. The stud 250, 252 cooperates with the groove 242 so as to follow the path formed by the groove 242 when the wheel 204, 206 rotates. The stud 250, 252 is therefore movable in the groove 242. In other words, a groove cam mechanism is used and in particular a differential cam transmission is used which contributes to the displacement of the jaw 208, 210.

It is therefore understood that the actuation mechanism 200 comprises one or more jaws 208, 210 mounted movable relative to the sleeve 202 so as to be translatable relative to at least one guide 226. The or each jaw 208, 210 further comprises one or more studs 250, 252 so that the at least one groove 242 of each wheel 204, 206 movably receives a stud 250, 252.

The mechanism 200 also comprises at least two drive shafts 212, 214, each mechanically connected to a motorisation element. The first drive shaft 212 is equipped with a first mechanical transmission element 254 cooperating with the mechanical transmission element 244 of the wheel 204 and the second drive shaft 214 is equipped with another first mechanical transmission element 254 cooperating with the mechanical transmission element 244 of the other wheel 206. In the example shown here, each of the mechanical transmission elements 254 of the drive shafts 212, 214 is a gear cooperating with the gears 244 of the wheels 204, 206.

Each shaft 212, 214 is housed in a generally cylindrical sheath 256 in which the shaft 212, 214 can move in rotation. The first mechanical transmission element 254 is located at one end of the sheath 256. A second mechanical transmission element 260 is located at the other end of the sheath 256. In this example, the elements 254 and 260 are gears.

In one embodiment, not shown here, the elements 254 and 260 may be pulleys. The element 254 may be a pulley driving a belt for actuating the mechanical transmission element 244 of a wheel 204, 206. In such a case, the mechanical transmission element 244 of a wheel 204, 206 is a pulley driven by the belt. The mechanical transmission element 260 may also be a pulley actuated by a belt.

In another embodiment, the mechanical transmission elements 244, 254, 260 may be gears and/or pulleys actuated by belt.

In another embodiment, not shown here, the mechanism 200 is identical to what has already been described above, except that the mechanism 200 is equipped with a single jaw 208, 210. In this embodiment, the jaw 208, 210 comprises a stud 250, 252 on each of its faces, such that the first stud 250 is movably mounted in the at least one groove 242 of the first wheel 204 and the second stud 252 is movably mounted in the at least one groove 242 of the other wheel 206.

The mechanism 200 described above can be housed in a compartment 300. This compartment 300 also allows the different elements of the actuation mechanism 200 to be maintained in place so that these elements interact with each other and contributes to the compactness of the device.

The compartment 300 comprises an upper shell 302 and a lower shell 318 designed to cooperate with each other.

The upper shell 302 further consists of an upstream portion 302a and a downstream portion 302b. Each portion 302a, 302b is monobloc and has a generally rectangular shape comprising an external face 304a, 304b and an internal face 306a, 306b within which a circular opening 308a, 308b is provided. Each portion 302a, 302b also comprises a cylindrical recess 310a, 310b on the internal face 304a, 304b in the axis of the opening 308a, 308b, designed to receive one of the wheels 204, 206. Each portion 302a, 302b comprises at its base a semi-circular recessed protuberance 312a, 312b extending in a plane perpendicular to the opening 308a, 308b and adapted to overlie the first gear 254 of a drive shaft 212, 214. The recessed segment of the protuberance 312a, 312b communicates with the recess 310a, 310b so that the first gear 254 cooperates with the gear 244 of the wheel 204, 206.

It is therefore understood that the diameter of the cylindrical recess 310a, 310b is substantially greater than or equal to the diameter of the wheels 204, 206. It is also understood that the upstream 302a and downstream 302b portions are mounted around the upstream 218 and downstream 220 ends of the sleeve 202 respectively. In other words, the diameter of the opening 308a of the upstream portion 302a is substantially equal to or greater than the diameter of the body 216 of the sleeve 202 and the diameter of the opening 308b of the downstream portion 302b is substantially equal to or greater than the diameter of the downstream end 220.

The downstream portion 302b also comprises at least two pins 314 on its internal face 306b and at least two other pins on its lower slice 316b, not visible in the figures. The upstream portion 302a also comprises at least two blind holes on its internal face 306a, although not visible in the figures, and at least two pins on its lower slice 316a. The pins 314 of the downstream portion 302b are configured to cooperate with blind holes located on the internal face 306a of the upstream portion 302a.

The lower shell 318 is a monobloc assembly comprising a base 320 and at least two protuberances 322. The base 320 is substantially planar and rectangular and further comprises an upper face 324 and a lower face 326. At least four blind holes 328 are provided in pairs on the upper face 324. At least four tenons 330, are equally distributed on the edges of the lower face 326 of the base 320.

The cylindrical protuberances 322 are located as projections of the lower face 326. Each of these protuberances 322 is recessed and open at both ends so that one end opens onto the upper face 324 of the base 320 through an orifice 332. The protuberances 322 are configured to receive the drive shafts 212, 214.

The upper shell 302 is mounted on the lower shell 318 so that the pins of each of the upstream and downstream portions 302a, 302b engage in the blind holes 328 in the base.

In this way, the actuation mechanism 200 is protected and maintained in place by the protective compartment 300. This allows the different elements to move within the compartment 300, making it easier to integrate them.

A receptacle 400 configured to receive the previously described compartment 300 may be attached to the end 500 of the apparatus. The receptacle 400 is also removable, i.e. it can be removed from the end 500.

The receptacle 400 comprises a hub 402 corresponding to the footprint of the lower shell 318 of the compartment 300 so that the compartment 300 can be snapped into place.

It is understood that this hub 402 comprises at least two orifices 404 designed for the passage of the cylindrical protuberances 322 and at least four mortises 406 designed to cooperate with the tenons 330 of the lower shell 318. The cross-section of the mortises 406 is substantially equal to or smaller than the cross-section of the tenons 330 so that the latter forcefully enter the mortises 406. In this way, the compartment 300 is secured to the receptacle 400. It is also understood that the compartment 300 is removable from the receptacle 400.

The receptacle 400 may further comprise at its base 408 a protective barrier, in the form of a cover, designed to cover and confine a portion of the apparatus, in particular the portion not carrying the module 600, so as to isolate it from the sterile field around the patient. This cover can be sterile.

In one embodiment, not shown here, the compartment 300 has a screw attachment means. In such a case, threaded through holes are substituted for the tenons 330 and mortises 406. However, such an attachment means makes the time needed to change tools longer than the clip-on solution described above.

In operation, a standard, off-the-shelf surgical instrument 100 can be inserted into the sleeve 202 of the actuation mechanism 200. In particular, the instrument 100 can be removed manually by the practitioner and replaced by another instrument, different from the first, during the surgical operation.

A motorisation element drives at least two drive shafts 502a, 502b, housed within the apparatus. The ends of these shafts 502a, 502b, which are not driven by the motorisation element, project from the end 500 and are each equipped with a mechanical transmission element 504a, 504b. These elements 504a, 504b are configured to cooperate with and transmit a rotational movement to the elements 260 of the drive shafts 212, 214 of the actuation mechanism 200. The drive shafts 212, 214 cooperate with the mechanical transmission elements 244 of the wheels 204, 206 and drive them in rotation about the longitudinal axis X.

The motorisation element can rotate the shafts 502a, 502b in either direction and each of the shafts 502a, 502b can rotate in a same or opposite direction. As a result, the wheels 204, 206 may rotate in the same or opposite direction.

Reference is now made to FIGS. 6 and 7 which illustrate drawings of cams generating desired movements for actuation of the surgical instrument 100.

In the example embodiments shown here, each wheel 204, 206 comprises two identical diametrically opposed grooves 242, or cams 242, but may also comprise one or more. Thus, the wheel 204 comprises the grooves 242a and the wheel 206 comprises the grooves 242b. In operation, the first wheel 204 and the second wheel 206 cooperate with at least one jaw 208, 210 such that the studs 250, 252 of the at least one jaw 208, 210 are both engaged with the cam 242a of the first wheel 204 and the cam 242b of the second wheel 206. The position of the studs 250, 252 of the jaw 208, 210 corresponds substantially to the intersection of a cam 242a of the first wheel 204 with the projection of a cam 242b of the second wheel 206 transposed on the same plane as the first wheel 204.

The simultaneous rotation of the movable wheels 204, 206 causes the cam 242 to be actuated and generates a movement of the jaws 208, 210. This movement is predetermined by the shape of the path of the cam 242 and the direction of rotation of the wheels 204, 206.

First Option: Rotation or Pinch

In FIGS. 6A to 6C, the cam 242a, 242b describes a non-concentric arc with the wheel 204, 206. A first end 1a, 1b of the cam 242a, 242b is located near the internal peripheral edge 234 of the wheel 204, 206 while a second end 2a, 2b of the cam is located near the external peripheral edge 236 of the wheel 204, 206. In other words, the distance between the groove 242a, 242b and the centre of the wheel 204, 206 varies along the groove 242a, 242b.

In this configuration, the cam 242a, 242b follows a spiral trajectory, defined by the equation:

$$r = a_0 + b\phi, \; b = \frac{a_1 - a_0}{2\pi n}, \; n \in \mathbb{R}[0, 1] \qquad \text{[Math. 1]}$$

Where r represents the position of the jaw 208, 210 in the spiral within the interval $[a_0, a_1]$ belonging to a real number, $\phi$ represents the angle and n represents the number of turns of the spiral.

The simultaneous rotation of each wheel 204, 206 in a given direction gives rise to a differential transmission whose operation is given by the following equations:

$$\rho = \frac{\theta_1 + \theta_2}{2}, \; \rho = n\eta, \; \eta \in \mathbb{R}[0, 1] \qquad \text{[Math. 2]}$$

$$\theta = (\theta_1 - \theta_2)\pi \qquad \text{[Math. 3]}$$

Where $\theta_1$ and $\theta_2$ represent the angular positions of the movable wheels 204, 206, $\theta$ is the angular position of the jaw 208, 210, $\rho$ is the radial position of the jaw, $\eta$ is the percentage of clamping of the jaw 208, 210 in the range $[a_0, a_1]$ allowed by the intersection of the spirals of the cams 242a, 242b.

This means that in the differential cam transmission system: the weighted sum of the rotations of the wheels 204, 206 ($\theta_1+\theta_2$), generates a first movement of the jaw 208, 210 relative to the predetermined shape of the cam 242 and that the weighted difference of the wheels 204, 206 ($\theta_1-\theta_2$), generates a second rotational movement of the jaw 208, 210 about the axis of rotation of the wheels 204, 206.

In other words, a selective displacement of the jaw 208, 210 is made possible. Indeed, a rotation of the wheels 204, 206 about the longitudinal axis X in opposite directions causes a radial translation of the jaws 208, 210, without causing a displacement of the jaws 208, 210 about the axis X. A rotation of the wheels 204, 206 in the same direction results in a displacement of the jaw 208, 210 about the longitudinal axis X. As the jaw 208, 210 is located between the guides 226, which are stationary mounted with respect to the sleeve 202, for example came from matter with the sleeve 202, its movement forces the sleeve 202 to follow an identical movement by way of drive. In other words, a rotation of the wheels 204, 206 in the same direction causes a rotation of the sleeve 202 and thus of the surgical instrument 100, thereby allowing to reorient the tool 108 being manipulated. Furthermore, the rotation of the wheels 204, 206 in the same direction does not cause any radial displacement of the jaw 208, 210.

In FIG. 6A, the jaws 208, 210 are in a position referred to as open where the stud 250, 252 of each jaw 208, 210 is at a distance L from the internal peripheral edge 234 of the wheels 204, 206 such that the jaw 208, 210 is between the external peripheral edge 236 and the internal peripheral edge 234.

A quarter turn rotation can be performed for each wheel 204, 206, in opposite directions as in FIG. 6B or in the same direction as in FIG. 6C.

With a simultaneous rotation of a quarter turn in opposite directions, the jaws 208, 210 are in a position referred to as closed, as shown in FIG. 6B, where the stud 250, 252 of each jaw is at a distance 1 from the internal peripheral edge 234. In this position, the jaws 208, 210 protrude from the edge and reduce the diameter of the circular space.

The jaws 208, 210 therefore move radially over a distance corresponding to the difference between the distance L and the distance 1. The jaws 208, 210 slide on the tracks 230 of the guides 226 and fit into the peripheral openings 232 of the sleeve 202. The radial translation of the jaws 208, 210 allows a pressure to be exerted on the surgical instrument 100 crimped in the sleeve 202. In particular, at the end of the translation, the jaw 208, 210 presses on the gripper 104 of the instrument, thereby allowing to actuate the surgical tool 108 as described in FIG. 1 above. This embodiment is therefore very useful when the surgical tool 108 is a pliers or pair of scissors.

With a simultaneous rotation of a quarter turn in the same direction, the jaws 208, 210 remain in their initial position, either open or closed, and do not displace radially. In contrast, the jaws 208, 210 are driven in rotation about the axis X as shown in FIG. 6C. It is understood that the rotation of the sleeve 202 may occur before or after the actuation of the surgical tool 108.

It should be noted that the shape of the cam shown here is not limiting. Indeed, the cam can adopt any shape leading to a trajectory allowing the radial translation or the rotation of at least one jaw.

For example, the cam may be in the form of a straight line with a first end of the line located in the vicinity of the internal peripheral edge 234 of the wheel 204, 206 while a second end of the line is located in the vicinity of the external peripheral edge 236 of the wheel 204, 206.

In another example, the cam can be continuous, i.e. the groove forms a loop. This loop may be substantially ellipsoidal or substantially star-shaped. In the case of a star-shape, the summit of each branch is the furthest position from the centre of the wheel 204, 206 while the hollow separating each branch is the closest position. This kind of loop configuration can be interesting when cyclic movements are required, as the frequency of the cycle can be determined by the pattern of the loop.

It is understood that the radial distance of the groove 242a, 242b with respect to the centre of the wheel 204, 206 is variable along the groove 242a, 242b. In other words, the groove 242a, 242b is not concentric with the wheel 204, 206.

Second Option: Rotation or Translation

In another embodiment, illustrated in FIGS. 7A to 7C, the cam 242 describes an arc concentric with the wheel 204, 206 and has a variable depth along this arc. In other words, the first 1a, 1b and second 2a, 2b ends of the cams 242a, 242b are located equidistant from the internal and external peripheral edges 234, 236 of the wheel 204, 206 respectively. It is therefore understood that the radial distance with respect to the centre of the wheel 204, 206 is constant along the groove 242a, 242b.

Furthermore, the depth of the cam 242a at the end 1a is greater than the depth of the cam 242a at the end 2a. In other words, a depth gradient is obtained between the two ends 1a and 2a of the cam 242a. The cam 242b is similar to the cam 242a, so the depth of the cam 242b at the end 1b is less than the depth of the cam 242b at the end 2b. A depth gradient is therefore also obtained between the two ends 1b and 2b of the cam 242b.

In this configuration, the cam 242a, 242b follows a circular trajectory whose depth oriented in the direction of the axis X is defined by the equation:

$$z = u_0 + v\phi, v = \frac{u_1 - u_0}{2\pi n}, n \in \mathbb{R}[0, 1] \qquad \text{[Math. 4]}$$

Where z represents the position of the jaw 208, 210 relative to the depth of the cam 242a, 242b within the range $[u_0, u_1]$ belonging to a real number, $\phi$ represents the angle and n represents the number of revolutions of the circular.

The differential transmission as described in the previous embodiment by the equations [Math. 2] and [Math. 3] also applies here, except that η is the percentage of translation of the jaw 208, 210 in the range $[u_0, u_1]$ allowed by the inclined planes of the cams 242a, 242b.

In other words, a selective displacement of the jaw 208, 210 is also made possible. Indeed, a rotation of the wheels 204, 206 about the axis X in opposite directions generates a longitudinal translation of the jaw 208, 210, without generating a displacement of the jaw 208, 210 about the axis X. As before, a rotation of the wheels 204, 206 in the same direction allows a rotation of the sleeve 202, without causing longitudinal displacement of the jaw 208, 210.

In this embodiment, the jaws 208, 210 are positioned in contact with the surgical instrument 100 and remain in this position during the various rotations due to the fact that the cams 242a, 242b each describe an arc of a circle concentric with the wheels 204, 206.

A simultaneous rotation of a quarter turn can be performed for each wheel 204, 206, in an opposite direction or in a same direction.

With a simultaneous rotation of a quarter turn in the same direction, the jaws 208, 210 are driven in rotation about the axis X. As previously described, the sleeve 202 rotates about its longitudinal axis X.

Reference is now made to FIGS. 7B and 7C which illustrate the positioning of the jaw 208, 210 along the cutting axis T in FIG. 7A.

In FIG. 7B, the centre of the jaw 208, 210 is in an initial position and is separated by a distance W from the face 238 of the wheel 204. The studs 250, 252 of the jaw 208, 210 are engaged in the cam 242a of the wheel 204 at the level of the end 2a and in the cam 242b of the wheel 206 at the level of the end 2b. During the simultaneous rotation of the wheels 204, 206, the studs 250, 252 of the jaw 208, 210 follow the relief, whose evolution is reversed, of the cams 242a, 242b.

In FIG. 7C, when the quarter turn rotation is complete, the studs 250, 252 are at the end 1a of the cam 242a and at the end 1b of the cam 242b. In addition, the centre of the jaw 208, 210 has displaced and is separated from the face 238 by a distance w, substantially less than the distance W.

Thus, with a simultaneous rotation of a quarter turn in an opposite direction, the jaws 208, 210 displace longitudinally, along axes parallel to the longitudinal axis X. The jaws 208, 210 can thus translate over a distance corresponding to the difference between the distance W and the distance w, and generate a sliding movement on the gripper 104.

It should be noted that the shape of the cam shown here is not limiting. Indeed, the cam can adopt any shape leading to a trajectory allowing the longitudinal translation or the rotation of at least one jaw.

Third Option: Rotation or Pinch with Translation

In another embodiment, the cam 242 describes a non-concentric arc with the wheel 204, 206 and has a variable depth along this arc. A first end 1a, 1b of the cam 242a, 242b is located in the vicinity of the internal peripheral edge 234 of the wheel 204, 206 while a second end 2a, 2b of the cam 242a, 242b is located in the vicinity of the external peripheral edge 236, and the depth of the cam 242a, 242b varies along the trajectory. In other words, this embodiment is a combination of the first two embodiments previously described and the cam 242a, 242b follows a trajectory as defined by the equations [Math. 1] and [Math. 4]. The cam thus follows a spiral trajectory in three dimensions.

In this case, η is at the same time the percentage of clamping of the jaw 208, 210 in the range $[a_0, a_1]$ as well as the percentage of translation of the jaw 208, 210 in the range

[$u_0$, $u_1$] allowed by the physical constraints imposed by the intersection of the cams 242a, 242b.

In other words, a selective displacement of the jaw 208, 210 is made possible. Indeed, a rotation of the wheels 204, 206 around the longitudinal axis X in opposite directions simultaneously generates a radial translation and a longitudinal translation of the jaw 208, 210, without generating a displacement of the jaw 208, 210 around the axis X. A rotation of the wheels 204, 206 in the same direction causes a displacement of the jaws 208, 210 about the longitudinal axis X, and thus of the sleeve 202 as explained above. Furthermore, the rotation of the wheels 204, 206 in the same direction does not cause any radial or longitudinal displacement of the jaw 208, 210.

This embodiment may be of interest in cases where the practitioner needs to operate a slide on the gripper 104 and not press it to actuate the tool 108. This is because a longitudinal translation of the slide is required. The simultaneous displacement of the jaw 208, 210 radially on the one hand and longitudinally on the other hand allows the gripper 104 to be gripped and the jaws 208, 210 to be displaced longitudinally on the slide which subsequently actuates the surgical tool.

The movement options described above involve a mechanism 200 equipped with two jaws 208, 210. It should be noted that the number of jaws 208, 210 is not limiting. The same result can be achieved with a mechanism 200 equipped with a single jaw 208, 210. In this embodiment, the jaw 208, 210 comprises a stud 250, 252 on each face thereof, such that the first stud 250 is movably mounted in the first groove 242a and the second stud 252 is movably mounted in the second groove 242b.

Reference is now made to FIG. 8 which shows another embodiment of the actuation mechanism 200.

In this embodiment, the actuation mechanism 200 is broadly similar to what has been described above. It comprises a sleeve 202, wheels 204, 206, at least one jaw 208, 210 equipped with one or more studs 250, 252 and drive shafts 212, 214. The wheels 204, 206, the at least one jaw 208, 210 and the drive shafts 212, 214 are similar and mounted as described above.

The sleeve 202 comprises an upstream end 218 and a downstream end 220 that are separable from each other. In other words, the sleeve 202 is not monobloc. The upstream end 218 comprises at least one first guide 262, stationary mounted with respect to the upstream end 218, for example came from matter with the end 218. The downstream end 220 comprises at least one second guide 264, stationary mounted relative to the downstream end 220, for example came from matter with the end 220.

The at least one first guide 262 of the upstream end 218 comprises a recess oriented in the direction of the downstream end 220. At least one through hole 266 is provided in the at least one first guide 262.

The at least one second guide 264 of the downstream end 220 comprises a stud 268 on a first face and a stud 270 on a second face, the stud 270 being configured to pass through the hole 266 of the at least one first guide 262. In addition, the at least one second guide 264 may axially engage the recess of the at least one first guide 262. It is understood that the dimensions of the guide 264 are substantially smaller than those of the guide 262 so that the guide 264 fits in adjusted manner into the recess of the guide 262.

The stud 268 of the guide 264 is configured to be movably mounted in a groove 242 of the wheel 204. The stud 270 is configured to be movably mounted in a groove 242 of the wheel 206.

In operation, the wheels 204, 206 are actuated as described above. In the example shown in FIG. 8, each wheel 204, 206 comprises two sets of grooves 242. In a first set of identical and diametrically opposed grooves 242, the radial distance of each groove 242 with respect to the centre of the wheel 204, 206 varies along the groove 242. In a second set of identical and diametrically opposed grooves 243, each groove 243 has a constant radial distance along the groove 243 with respect to the centre of the wheel 204, 206. Each groove 243 may have a depth gradient along the groove 243.

For each wheel 204, 206, the first set of grooves 242 cooperates with the at least one jaw 208, 210 by means of the studs 250, 252 and the second set of grooves 243 cooperates with the at least one second guide 264 by means of the studs 268, 270.

A rotation of the wheels 204, 206 in a same direction results, as previously described, in a rotation of the sleeve 202 about the longitudinal axis X.

The simultaneous rotation of the wheels 204, 206 in one of the opposite directions cause the actuation of the cams 242, 243 and generates a simultaneous movement of the jaws 208, 210 and the downstream end 220 of the sleeve 202. The at least one jaw 208, 210 translates radially, as previously described in the first option, to exert a pressure on the gripper 104 of the surgical instrument 100. The downstream end 220 of the sleeve 202 translates longitudinally, as described previously in the second option. It is understood that this embodiment is a variant of the third option described above.

The advantage of this configuration is that it can accommodate an instrument 100 whose head 112 translates when a pressure is exerted to the gripper 104. Indeed, a translation of the head 112 requires that the downstream end 220 of the sleeve 202, which holds the instrument 100 forward, accompany the translation movement.

Reference is now made to FIG. 9 which illustrates another embodiment of the mechanism 200. In this embodiment, one or more parts 280 are stationary mounted with respect to the sleeve 202. The or each part 280 may, for example, came from matter with the sleeve 202. The or each part 280 comprises one or more studs 268, 270, extending along the longitudinal axis X of the sleeve 202, such that the at least one groove 242 of each wheel 204, 206 movably receives a stud 268, 270.

In the example shown in FIG. 9, the part 280 is equipped with a stud 268, 270 on each of its faces. The stud 268 faces the wheel 204 and the stud 270 faces the wheel 206. It is therefore understood that the stud 268 engages in the groove 242 of the wheel 204 and the stud 270 engages in the groove 242 of the wheel 206. At least one spacer 290 may be mounted in the same plane, perpendicular to the longitudinal axis X of the sleeve 202, as the part 280. This spacer 290 maintains a stationary axial spacing between the wheels 204, 206. Furthermore, the thickness of the spacer 290 is substantially greater than the thickness of the part 280.

In operation, the surgical instrument 100 is inserted into the sleeve 202. Each wheel 204, 206 comprises at least one groove 242 as described in the second previous option, i.e. with a variable depth along the groove 242 and a constant angular position with respect to the centre of the wheel 204, 206. In the same way as in the second option, the rotation of the wheels 204, 206, in particular in opposite directions, generates a longitudinal translation of the sleeve 202 driven by the part 280.

It is understood that the longitudinal translation of the sleeve 202 allows the surgical instrument 100 to be translated. This may be of particular interest where the instrument 100 comprises a syringe and a puncture action is required.

In the end, with the different embodiments described above, several studs extending along the longitudinal axis X are provided on the or each part, on some parts only (see the case of FIGS. 4, 5 and 9 where the studs are either on the guides or on the jaws), or even distributed over the different parts (see the case of FIG. 8 with studs on both the guides and the jaws).

The receptacle 400, the protective cover, the protective compartment 300 and the various elements composing the actuation mechanism 200 listed above may be single-use and sterile. A plastic material can be used. This has the primary advantage of keeping a sterile environment around the patient during the procedure, keeping the patient free from infection. As the elements are interchangeable and single-use, they can easily be mounted, in particular by clipping, on the end of the apparatus at the beginning of the surgical operation and be discarded once the operation is over. The compartment 300 comprising the mechanism 200 can be changed during the surgery if the use of a particular mechanism 200 as described above is required. The second advantage is the low cost of these plastic elements, which makes them easily replaceable elements.

In addition, the mechanism 200 allows the surgical instrument 100 to move with several degrees of freedom, in rotation and in translation in particular, but also allows to exert a pressure or a sliding on a gripper 104 of the instrument 100. This confers the advantage that a wide range of standard, off-the-shelf surgical instruments can be used without requiring a hardware modification of the latter.

Finally, the actuation mechanism 200 is simple in its configuration and does not occupy a large volume due to the fact that the motorisation element, allowing its implementation, is offset in a portion external to the module 600, a stationary portion or one that does not require complex movements. Indeed, the increased compactness of the mechanism 200 allows for a reduction in workspace clutter, allowing the practitioner to keep the patient in his or her field of view and, in addition, allows for the use of other apparatus in the vicinity of the invention such as a microscope used in the conventional vitreoretinal surgery or other apparatus similar to the invention described above.

It should also be noted that, although not part of the invention, the apparatus described above can be used in combination with a control interface and/or a software module which translates the movements of the interface into movement of the actuation mechanism. In particular, the control interface allows the movements of the surgeon to be reproduced with great precision, allowing him or her to act at a distance from the patient.

The invention claimed is:

1. An actuation mechanism for a surgical instrument, comprising:
   a sleeve, equipped with a longitudinal axis, configured to receive the surgical instrument and comprising one or more parts extending substantially in a plane perpendicular to said longitudinal axis, a plurality of studs extending along the longitudinal axis being provided on each of the one or more parts, on some parts only, or distributed over the different parts;
   at least two wheels, mounted on the sleeve on either side of said part or parts along said longitudinal axis, each wheel being equipped with at least one groove and a mechanical transmission element, said at least one groove of each wheel movably receiving one of said plurality of studs in said groove;
   at least two drive shafts, including a first drive shaft equipped with a first mechanical transmission element cooperating with the mechanical transmission element of one of the two wheels and a second drive shaft (214) being equipped with another first mechanical transmission element cooperating with the mechanical transmission element of the other of the two wheels.

2. The actuation mechanism of claim 1, wherein the sleeve comprises an internal abutment extending radially at a level of a first end of said sleeve, and flexible tongues extending axially at a level of a second end of said sleeve.

3. The actuation mechanism according to claim 1, wherein said at least one part is a jaw, mounted between guides so as to be translatable relative to said guides, said guides being mounted stationary relative to the sleeve.

4. The actuation mechanism according to claim 3, wherein the mechanical transmission element is a gear or a belt driven pulley.

5. The actuation mechanism according to claim 1, wherein said at least one part is a guide, stationary mounted with respect to the sleeve.

6. The actuation mechanism (200) according to claim 1, wherein the groove has a radial distance with respect to a center of the wheel that varies along said groove.

7. A method for implementing an actuation mechanism according to claim 6, said method being carried out outside the patient, wherein a rotation in opposite directions of the wheels causes a radial translation of at least one part so that said part exerts a pressure on the surgical instrument.

8. A method for implementing an actuation mechanism according to claim 6, said method being carried out outside the patient, wherein a rotation of the wheels in opposite directions simultaneously causes a longitudinal translation and a radial translation of at least one part so that said part exerts a pressure on the surgical instrument while displacing longitudinally along said instrument.

9. The actuation mechanism according to claim 1, wherein the groove has a radial distance with respect to a center of the wheel, which is constant along said groove.

10. A method for implementing an actuation mechanism according to claim 9, said method being carried out outside the patient, wherein a rotation in opposite directions of the wheels causes a longitudinal translation of at least one part along the surgical instrument.

11. The actuation mechanism according to claim 1, wherein the groove has a variable depth along said groove.

12. The actuation mechanism according to claim 1, wherein each wheel comprises at least one first groove having a radial distance with respect to a center of the wheel which varies along said first groove and having a variable depth along said first groove, and at least one second groove, different from said first groove having a radial distance with respect to the center of the wheel which is constant along said second groove and having a variable depth along said second groove.

13. A method for implementing an actuation mechanism according to claim 12, said method being carried out outside the patient, wherein a rotation of the wheels in opposite directions simultaneously causes a longitudinal translation of at least one part along the surgical instrument and a radial translation of at least one other part such that said other part exerts a pressure on the surgical instrument.

14. A module which comprises an actuation mechanism according to claim 1, said mechanism being housed in a protective compartment, maintaining elements of said actuation mechanism in interaction.

15. The module according to claim 14, comprising a removable receptacle configured to receive the protective compartment, said receptacle being attached to one end of an apparatus.

16. The module according to claim 15, wherein at least two parallel drive shafts, mechanically connected to a motor, are located projecting from said end, each shaft being configured to cooperate with a second mechanical transmission element of one of said at least two drive shafts of the actuation mechanism.

17. The module according to claim 15, wherein a protective cover is integrated into the receptacle such that said cover surrounds a portion opposite the module.

18. The module according to claim 1, wherein the receptacle, the compartment, the mechanism and the cover are sterile single-use equipment.

19. A method for implementing an actuation mechanism according to claim 1, said method being carried out outside the patient, wherein a rotation in a same direction of the wheels causes a rotation of the sleeve about the longitudinal axis.

* * * * *